(12) United States Patent
Plishka et al.

(10) Patent No.: US 7,922,690 B2
(45) Date of Patent: Apr. 12, 2011

(54) CURABLE MATERIAL DELIVERY DEVICE

(76) Inventors: Michael Plishka, Lake Villa, IL (US); Brian Ruffner, Antioch, IL (US); Evan Linderman, Northbrook, IL (US); John Krueger, Muskego, WI (US)

( * ) Notice: Subject to any disclaimer, the term of this patent is extended or adjusted under 35 U.S.C. 154(b) by 1313 days.

(21) Appl. No.: 11/359,184

(22) Filed: Feb. 22, 2006

(65) Prior Publication Data

US 2007/0198024 A1    Aug. 23, 2007

(51) Int. Cl.
*A61F 2/00*    (2006.01)

(52) U.S. Cl. ........................................ 604/93

(58) Field of Classification Search ............... 604/187; 606/92, 93, 260, 279, 297
See application file for complete search history.

(56) References Cited

U.S. PATENT DOCUMENTS

| | | | |
|---|---|---|---|
| 5,306,277 A | 4/1994 | Bryant et al. | |
| 5,830,188 A | 11/1998 | Abouleish | |
| 6,099,532 A | 8/2000 | Florea | |
| 6,176,607 B1 | 1/2001 | Hajianpour | |
| 6,348,055 B1 * | 2/2002 | Preissman | 606/94 |
| 6,383,190 B1 | 5/2002 | Preissman | |
| 6,547,432 B2 | 4/2003 | Coffeen et al. | |
| 6,592,559 B1 | 7/2003 | Pakter et al. | |
| 2002/0010472 A1 | 1/2002 | Kuslich et al. | |
| 2004/0204715 A1 | 10/2004 | Evans et al. | |
| 2005/0124997 A1 | 6/2005 | Pajunk et al. | |
| 2005/0150911 A1 * | 7/2005 | Bach | 222/209 |
| 2007/0118142 A1 * | 5/2007 | Krueger et al. | 606/92 |
| 2007/0142842 A1 * | 6/2007 | Krueger et al. | 606/92 |
| 2007/0197971 A1 * | 8/2007 | Krueger et al. | 604/164.01 |

* cited by examiner

*Primary Examiner* — Nicholas D Lucchesi
*Assistant Examiner* — Diva Ranade
(74) *Attorney, Agent, or Firm* — Brinks Hofer Gilson & Lione

(57) ABSTRACT

An apparatus and method for introducing material into an injection site of a patient is disclosed. The device includes a cannula and a carrier. The cannula is inserted into an injection site of a patient. The carrier is connected to an injector containing a volume of material. Material may be pre-loaded into the carrier so that the material is delivered to a distal end of the carrier from the injector and the carrier is thus pre-loaded with material. A portion of the distal end of the pre-loaded carrier is inserted into the cannula and material is delivered to an injection site.

25 Claims, 10 Drawing Sheets

_US 7,922,690 B2_

CURABLE MATERIAL DELIVERY DEVICE

TECHNICAL FIELD

The present invention relates to devices and methods for stabilizing bone structures. More particularly, it relates to devices, systems and methods for delivering a curable, stabilizing material into a bone structure.

BACKGROUND INFORMATION

Surgical intervention at damaged or compromised bone sites has proven highly beneficial for patients, for example patients with back pain associated with vertebral damage.

Bones of the human skeletal system include mineralized tissue that can generally be categorized into two morphological groups: "cortical" bone and "cancellous" bone. Outer walls of all bones are composed of cortical bone, which has a dense, compact bone structure characterized by a microscopic porosity. Cancellous or "trabecular" bone forms the interior structure of bones. Cancellous bone is composed of a lattice of interconnected slender rods and plates known by the term "trabeculae."

During certain bone procedures, cancellous bone is supplemented by an injection of a palliative (or curative) material employed to stabilize the trabeculae. For example, superior and inferior vertebrae in the spine can be beneficially stabilized by the injection of an appropriate, curable material (e.g., PMMA or other bone curable material). In other procedures, percutaneous injection under computed tomography (CT) and/or fluoroscopic guidance of stabilization material into vertebral compression fractures by, for example, transpedicular or perpendicular approaches, has proven beneficial in relieving pain and stabilizing damaged bone sites. Other skeletal bones (e.g., the femur) can be treated in a similar fashion. In any regard, bone in general, and cancellous bone in particular, can be strengthened and stabilized by a palliative injection of bone-compatible material.

Using a vertebropasty as a non-limiting example, a conventional technique for delivering the bone stabilizing material entails placing a cannula with an internal stylet into the desired injection site. The cannula and stylet are used in conjunction to pierce the cutaneous layers of a patient above the hard tissue to be supplemented, then to penetrate the hard cortical bone of the vertebra, and finally to traverse into the softer cancellous bone underlying the cortical bone. Once positioned in the cancellous bone, the stylet is then removed leaving the cannula in the appropriate position for delivery of curable material to the trabecular space of the vertebra to reinforce and solidify the damaged hard tissue.

According to one method in the prior art, curable material, is introduced into an end of the cannula for delivery into the vertebra using a 1 cc syringe. A 1 cc syringe is used because it generates the high pressures required to the force curable material through the cannula and into the vertebra. A disadvantage of a 1 cc syringe is that an amount of curable material required for the procedure is larger than 1 cc. As a result, it is required to sterilely reload the syringe several times during the procedure. This increases time and complexity of the procedure and increases the risk of radiation exposure to the physician.

An improved prior art procedure uses a curable material injector loaded with a relatively larger volume of curable material. The injector is connected to an end of the cannula via a non-compliant supply tube. Pressure created at the injector pushes a column of curable material through the supply tube and into the cannula. Curable material is then delivered from the cannula into the trabecular space of the vertebra. Although an improvement over the use of a syringe, the method has several disadvantages.

The method results in less control for the physician because the flow of curable material through the cannula has been found to be somewhat unpredictable. A column of curable material is pushed by substantial pressure over a distance, creating a pressure head in the column. When the curable material column reaches the end of the cannula, physicians have experienced that the curable material can burst into the trabecular space, depositing an uncontrolled volume of curable material in an uncontrolled manner. Further, the transfer of curable material from the injector to the vertebra can only begin after the supply tube is connected to the cannula. A significant amount of time can elapse while the column of curable material is advanced through the supply tube and cannula.

Moreover, during a long procedure, curable material can begin to set inside of the cannula. After the desired amount of curable material is deposited in the vertebra, the cannula is removed at the completion of the procedure. The curable material that was in the cannula that may have begun to set may remain attached to the core of curable material in the bone. As the cannula is removed, the curable material may break inside of the cannula instead of at the tip of the cannula and leave a "spike" of curable material protruding from the vertebra.

There exists a need in the medical device field for an improved subcutaneous bone material delivery system. The present invention provides an efficient device and method of introducing curable material, or other material, into a bone structure in a controlled manner.

BRIEF SUMMARY

One aspect of the present invention is directed to an apparatus for introducing material into an injection site of a patient. The apparatus includes a cannula defining a lumen. The apparatus also includes a carrier for delivering material from an injector to an injection site. The carrier defines a lumen and includes a supply section operable to receive curable material, and an inner section having an axis and defining a tip section operable to direct material in a direction that is not coaxial with the axis of the inner section. In the apparatus, the carrier is releasably attachable with the cannula, and at least a portion of the inner section is located within the lumen of the cannula.

In another aspect of the present invention, an apparatus is provided for introducing material into an injection site of a patient. The apparatus has an injector containing a volume of material, a cannula having an elongated portion defining a lumen wherein an end of the elongated portion is for positioning within the injection site and a carrier defining a lumen between the injector and the injection site. The carrier further includes a supply tube having a first end adaptable for connecting the supply tube with the injector and receive material from the injector and a second end. The carrier also includes a connector attaching the carrier with the cannula. The connector also defines a chamber. The carrier also includes an inner tube having a first end and a second end, wherein the connector connects the second end of the supply tube with the first end of the inner tube via a chamber such that the supply tube, chamber and inner tube form a lumen having a substantially smooth transition from the supply tube to the inner tube. In the apparatus, at least a portion of the inner tube is located within the lumen of the elongated portion of the cannula.

In yet another aspect of the present invention, a method of delivering material to the injection site is provided. The method includes a step of inserting a cannula defining an elongated lumen into an injection site. The method also includes a step of connecting a carrier defining a lumen with an injector containing a volume of material. The method further includes a step of pre-loading the lumen of the carrier with the material so that the material is delivered to a distal end of the carrier from the injector, wherein the carrier is thus pre-loaded with material. The method also includes a step of inserting at least a portion of the distal end of the pre-loaded carrier into the elongated lumen of the cannula and delivering material to an injection site.

In another aspect of the present invention, a method of delivering material to the injection site is provided. The method includes a step of inserting a cannula defining an elongated lumen into an injection site. The method also includes a step of connecting a carrier with an injector containing a volume of material, said carrier defining a lumen and comprising an inner section distal from the injector. The method further includes a step of inserting at least a portion of the distal inner section of the carrier into the elongated lumen of the cannula. The method also includes a step of transmitting material from the injector through the lumen of the carrier wherein curable material is also transmitted through the distal inner section. The method finally includes a step of delivering material to an injection site.

Advantages of the present invention will become more apparent to those skilled in the art from the following description of the preferred embodiments of the invention which have been shown and described by way of illustration. As will be realized, the invention is capable of other and different embodiments, and its details are capable of modification in various respects. Accordingly, the drawings and description are to be regarded as illustrative in nature and not as restrictive.

DETAILED DESCRIPTION OF THE DRAWINGS AND THE PRESENTLY PREFERRED EMBODIMENTS

Figure 1:
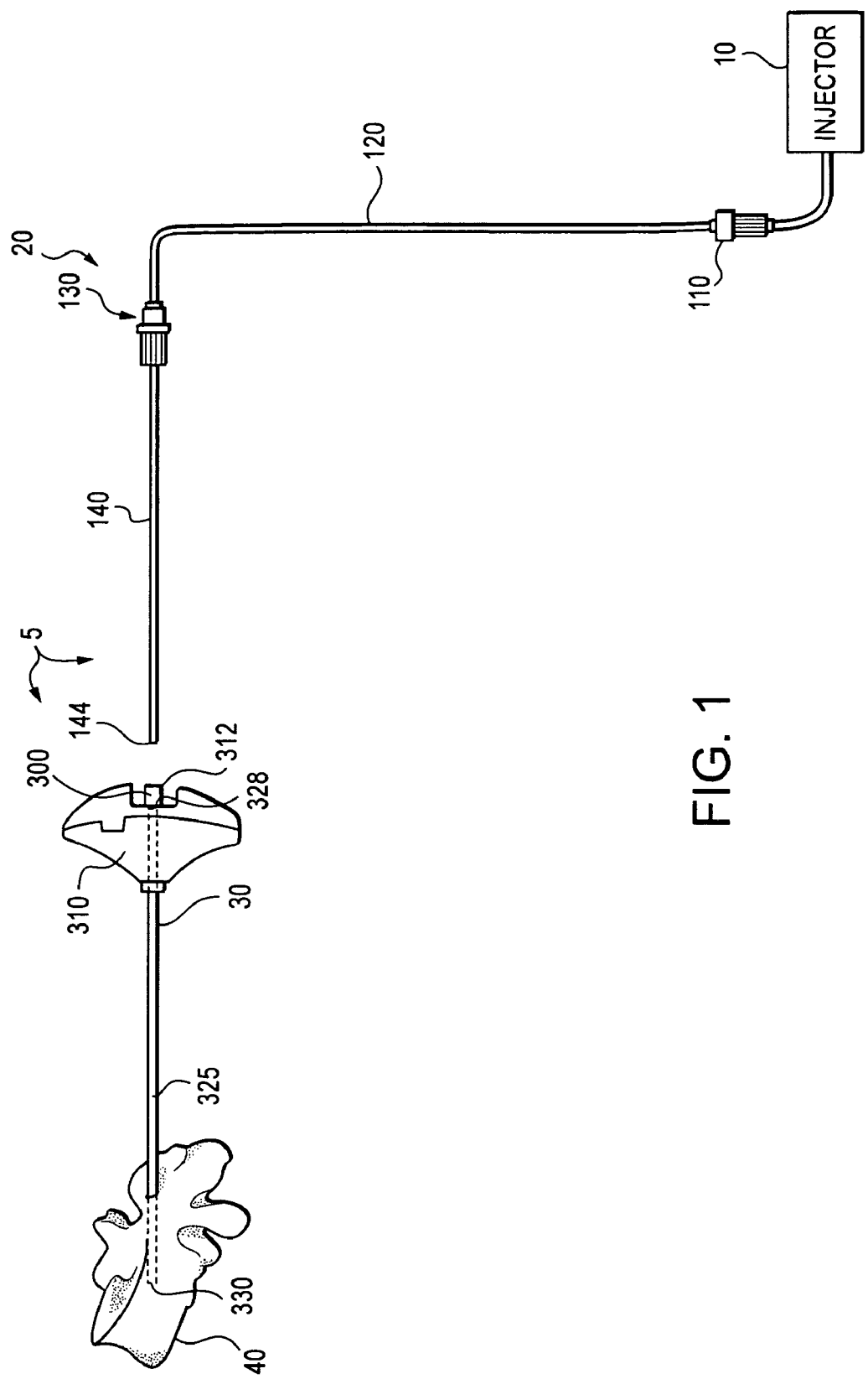
FIG. 1 is a perspective view of the curable material delivery device according to a preferred embodiment of the present invention prior to insertion of the inner section into the cannula.

FIG. 1 illustrates components of an intraosseous, curable material delivery system 5 according to principles of the present invention. The curable material delivery system 5 according to a preferred embodiment of the present invention has an injector 10, a carrier assembly 20 connected to the injector 10 via an injection connector 110 and a cannula 30 for insertion into a bone site of interest in a patient. In the embodiment depicted in FIG. 1, the bone site of interest is a vertebra 40.

Details on the various components are provided below. In general terms, however, a portion of the carrier assembly 20 is sized to be slidably disposed within the cannula 30 that otherwise serves to form and/or locate a desired injection site within a bone. Once positioned within the cannula, the carrier assembly 20 is employed to inject a curable, bone stabilizing material into the delivery site. The system 5 can be used for a number of different procedures, including, for example, vertebroplasty and other bone augmentation procedures in which curable material is delivered to a site within bone, as well as to remove or aspirate material from a site within bone.

The system 5, and in particular the carrier assembly 20, is highly useful for delivering a curable material in the form of a bone curable material. The phrase "curable material" within the context of the substance that can be delivered by the system/device of the invention described herein is intended to refer to materials (e.g., composites, polymers, and the like) that have a fluid or flowable state or phase and a hardened, solid or cured state or phase. Curable materials include, but are not limited to injectable bone cements (such as polymethylmethacrylate (PMMA) bone curable material), which have a flowable state wherein they can be delivered (e.g., injected) by a cannula to a site and subsequently cure into hardened curable material. Other materials, such as calcium phosphates, bone in-growth material, antibiotics, proteins, etc., could be used in place of or to augment, bone cement (but do not affect an overriding characteristic of the resultant formulation having a flowable state and a hardened, solid or cured state). This would allow the body to reabsorb the curable material or improve the clinical outcome based on the type of filler implant material.

The injector 10 may typically comprise a chamber filled with a volume of curable material and uses any suitable injection system or pumping mechanism to transmit curable material out of the injector and through the carrier assembly 20. Typically, a hand injection system is used where a physician applies force by hand to an injector. The force is then translated into pressure on the curable material to flow out of the chamber. A motorized system may also be used to apply force.

A cannula 30 is provided to be positioned in an injection site for delivery of curable material therein. The cannula 30 is preferably made of a surgical grade of stainless steel, but may be made of known equivalent materials which are both biocompatible and substantially non-compliant at operating pressures described herein. The cannula 30 defines a lumen 325 to allow the stylet (not shown), carrier assembly 20, and other equipment to pass through the cannula 30. Preferably, at least a distal end 330 of the cannula 30 is radiopaque. The cannula 30 has an inside diameter which is only slightly larger than the outside diameter of the stylet. The distal end 330 of the cannula 30 is preferably beveled to ease the penetration of the cannula through the cutaneous and soft tissues, and especially through the hard tissues.

Surrounding the proximal end 328 of the cannula 30 is a handle 310 for manipulating the cannula 30 and connecting the cannula 30 with carrier assembly 20 via a handle connector 312. Preferably, handle connector 312 has a Luer-lock type of connector, but other known connecting mechanisms may be successfully interchanged, e.g., a conventional threaded hole, a thread and locking nut arrangement, etc. Cannulas may be of standard lengths and diameters. A cannula may be about 4 cm to about 20 cm long and is preferably 12 cm long. Additionally, with respect to the cannula diameter, the cannula may be about 1.2 mm in outer diameter (18 gauge) with a wall thickness of about 0.216 mm to about 5.2 mm in outer diameter (6 gauge) with a wall thickness of about 0.381 mm, and is preferably about 3.1 mm in outer diameter (11 gauge) with a wall thickness of about 0.33 mm or about 2.1 mm in outer diameter (13 gauge) with a wall thickness of about 0.305 mm.

Figure 2:
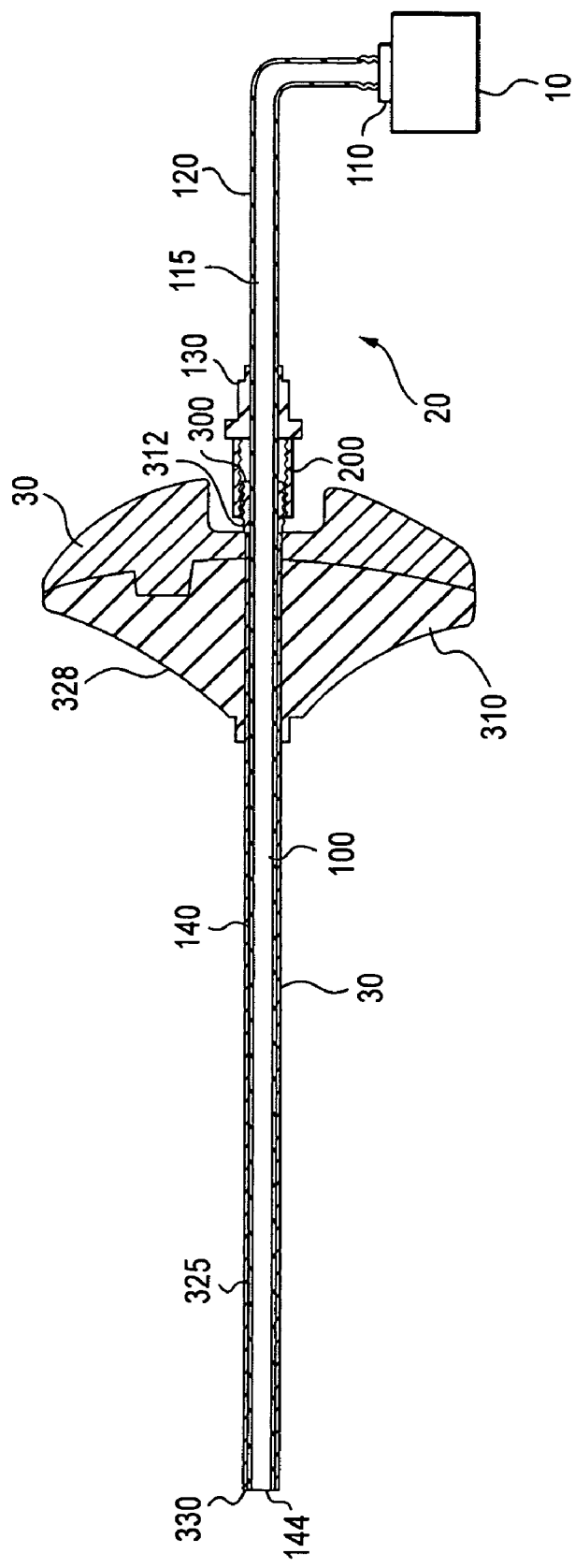
FIG. 2 is a cross-section view of the curable material delivery device according to a preferred embodiment of the present invention after insertion of the inner section into the cannula.

The carrier assembly 20 provides a passageway for curable material to travel from the injector 10 to an injection site, such as a vertebra 40. With reference to FIG. 2, carrier assembly 20 preferably defines a lumen 100 from the injection connector 110 to its terminal end 144 positioned inside of a patient. According to one preferred embodiment, the carrier assembly 20 comprises an injection connector 110, a cannula connector 130 and a transfer body 115. The transfer body 115 further comprises a supply section 120 and an inner section 140. The injection connector 110 is preferably a Luer-lock type of connector, but other known connecting mechanisms suitable for medical applications may be successfully interchanged.

The cannula connector 130 is fixedly attached to the transfer body 115 and connects the carrier assembly 20 with the cannula 30 and cannula handle 310. According to a preferred embodiment, the cannula connector 130 contains a Luer-lock threaded fitting 200 for connection with a Luer-lock threaded fitting 300 of the cannula 30 to allow the carrier assembly 20 and cannula 30 to be removably detachable.

The transfer body 115 is preferably a single tubular structure that defines lumen 100. Due to the operating pressures required to transfer curable material through the carrier assembly 20, the transfer body 115 is preferably made of a non-compliant material such as polyetheretherketone (PEEK). Other suitable materials include aluminum or wire reinforced plastic. The supply section 120 of the transfer body 115 is operable to receive curable material from the injector 10 and is generally defined by the section of the transfer body 115 between the injector 10 and the cannula connector 130. The inner section 120 of the transfer body 115 is operable to deliver curable material to an injection site and is generally defined by the section of the transfer body 115 between the cannula connector 130 and the terminal end 144 of the carrier assembly 20 for positioning within the patient. At least a portion of the inner section 140 is adapted to be inserted into the cannula 30. The inner section 140 must therefore have an outer diameter that is smaller than the inner diameter of the cannula 30; however, the outer diameter should not be so small so as to allow curable material to travel around the outside of the inner section 140 and back into the cannula 30. Preferably the clearance between the inner diameter of the cannula 30 and the outer diameter of the inner section 140 is within a range of about 1 to 30 thousandths of an inch and is more preferably no more than about 5 thousands of an inch.

Additionally, according to a preferred embodiment the distal end 330 of the cannula 30 extends beyond the terminal end 144 of the inner section 140 such that the terminal end 144 of the inner section 140 is at a length from the distal end 330 of the cannula 30 that is less than 50% of the length of the cannula 30. According to another preferred embodiment, the terminal end 144 of the inner section 140 is substantially even with the distal end 330 of the cannula 30. One skilled in the art will also understand that an inner section 140 that extends beyond the distal end 330 of the cannula 30 may also be used as long as the inner section 140 fits within the injection site and dispenses curable material effectively.

One skilled in the art will appreciate that although this embodiment uses a single tube for delivering curable material to the patient, the single tube may be manufactured to have different diameters at different sections of the tube.

Figure 3:
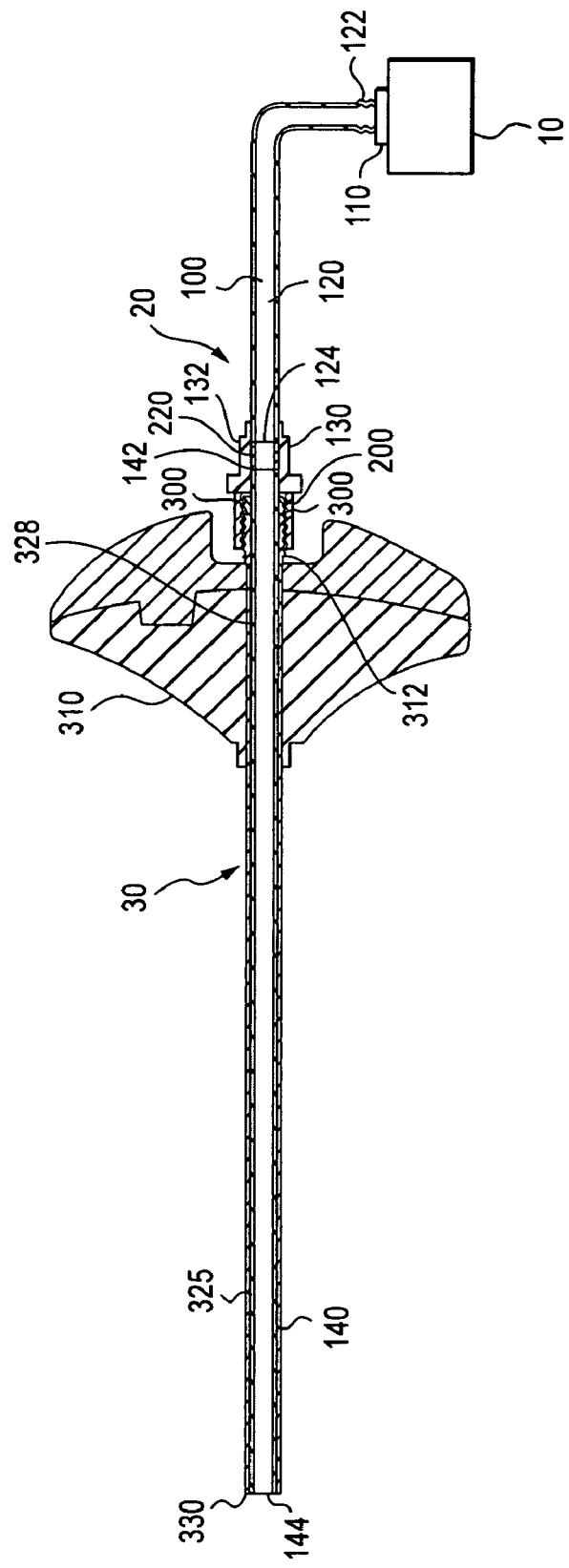
FIG. 3 is a cross-section view of the curable material delivery device according to another preferred embodiment of the present invention after insertion of the inner tube into the cannula.

With reference to FIG. 3, in another preferred embodiment, the supply section 120 and inner section 140 may be separate structures that are connected at the cannula connector 130. In this embodiment, preferably the supply section 120, cannula connector 130 and inner section 140 define the lumen 100. The supply section 120 has a first end 122 and second end 124 and is preferably a tubular structure that defines a portion of the lumen 100. Due to the operating pressures required to transfer curable material through the carrier assembly 20, the supply section 120 is preferably made of a non-compliant material such as polyetheretherketone (PEEK) or other polymer. Other suitable materials include aluminum or wire reinforced plastic. The second end 124 of the supply section 120 connects with a first end 132 of the cannula connector 130.

The inner section 140 comprises a first end 142 connected with the cannula connector 130 and a terminal end 144 for positioning within the patient to deliver curable material to an injection site. The inner section 140 is adapted to be inserted into the cannula and preferably extends from the cannula connector 130 to the injection site. Due to the operational pressures applied with injecting curable material, the inner section 140 is preferable made of a non-compliant material and is more preferably made of polyetheretherketone (PEEK) or aluminum. The inner section 140 must therefore have an outer diameter that is smaller than the inner diameter of the cannula 30; however, the outer diameter should not be so small so as to allow curable material to travel around the outside of the inner section 140 and back into the cannula 30. Preferably the clearance between the inner diameter of the cannula 30 and the outer diameter of the inner section 140 is within a range of about 1 to 30 thousandths of an inch and is more preferably no more than about 5 thousands of an inch. The supply section 120 and the inner section 140 may be made of the same or different materials.

Additionally, according to a preferred embodiment the distal end 330 of the cannula 30 extends beyond the terminal end 144 of the inner section 140 such that the terminal end 144 of the inner section 140 is at a length from the distal end 330 of the cannula 30 that is less than 50% of the length of the cannula 30. According to another preferred embodiment, the terminal end 144 of the inner section 140 is substantially even with the distal end 330 of the cannula 30. One skilled in the art will also understand that an inner section 140 that extends beyond the distal end 330 of the cannula 30 may also be used as long as the inner section 140 fits within the injection site and dispenses curable material effectively.

In this embodiment, in addition to connecting the carrier assembly 20 with the cannula 30, the cannula connector 130 also connects the supply section 120 with the inner section 140. According to a preferred embodiment, the supply tube 120 connects with the cannula connector 130 via a Leur-lock type of connector 210, but other known connecting mechanisms suitable for medical applications may be successfully interchanged. The cannula connector 130 further comprises a second Luer connection 312 for connecting the inner section 140 with the cannula connector 130.

Figure 4:
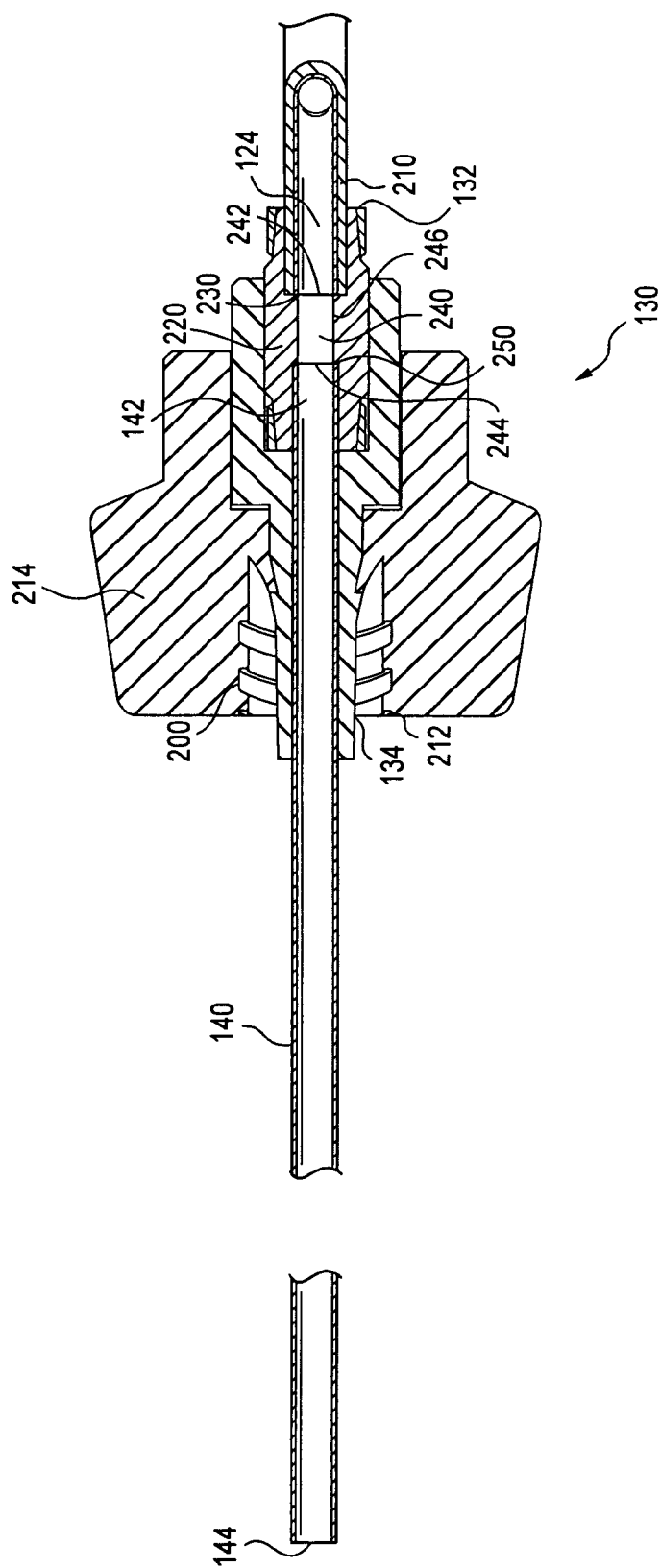
FIG. 4 is a cross-section of the connection between the supply tube and the cannula according to a preferred embodiment of the present invention.

With reference to FIG. 4, the cannula connector 130 preferably comprise a flangeless adapter 220. Flangeless adapter 220 provides a precise and smooth transition from the supply section 120 to the inner section 140. It has been found that disruptions in the walls defining the lumen 100, such as at abrupt transitions in fittings or connections, can cause curable material within the lumen 100 to prematurely set and potentially plug the line. As a result, a smooth transition at fittings or connections between lines advantageously delivers curable material to the patient.

Preferably, flangeless adapter 220 defines a first radial lip 230, a chamber 240, and a second radial lip 250. The chamber 240 further defines an input end 242, an output end 244 and a transition region 246. To effect a precise and smooth transition from the supply section 120 to the chamber 240, the second end of the supply section 124 abuts with the first radial lip 230 at the input end 242 of the chamber 240. The input end 242 of the chamber has an inner diameter that is substantially the same inner diameter of the supply section 120. Similarly, the first end 142 of the inner section 140 abuts with the second radial lip 250 at the output end 244 of the chamber 240. The output end 244 of the chamber 240 has an inner diameter that that is substantially the same as the inner diameter of the inner section 140. It will thus be appreciated that a precise and smooth transition between the supply section and the inner section is achieved.

In the embodiment depicted in FIG. 4, the supply section 120 and the inner section 140 have the same inner diameter. As a result the input end 242, transition region 246 and output end 244 of the chamber also have the same diameter. In another preferred embodiment, the supply section 120 and the inner section 140 may have different inner diameters. Accordingly, the input end 242 and output end 244 of the chamber 240 will also have different inner diameters. In this embodiment, the transition region 246 of the chamber 240 is tapered to smoothly transition the chamber 240 from one diameter to the other.

It has been observed that the application of curable material is more controllable where the downstream pathway of the curable material is more narrow than the upstream pathway. As a result, according to a preferred embodiment, the inner diameter of the inner section 140 is smaller than the inner diameter of the supply section 120. In this preferred embodiment, the transition region 246 will preferably smoothly transition the chamber 240 from a larger diameter at the input end 242 of the chamber to a smaller diameter at a output end 244 of the chamber. It is important to keep in mind that abrupt transitions in connections should be avoided to prevent plugging by the curable material. The flangeless adapter 220 is preferably made of a material that can withstand the operational pressures such as polyetheretherketone (PEEK) or other polymers.

Figure 5:
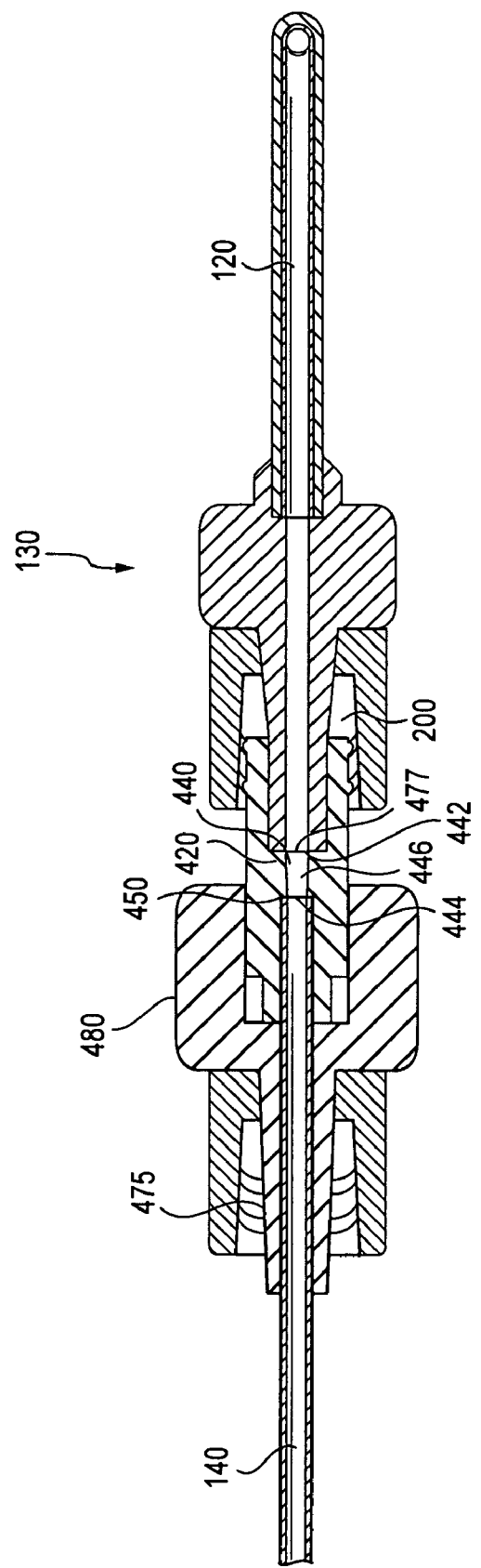
FIG. 5 is a cross-section of the connection between the supply tube and the cannula according to a another preferred embodiment of the present invention.

With reference to FIG. 5, another embodiment of the cannula connector is presented. In this embodiment the supply section 120 and the inner section 140 are conveniently detachable from each other such that different inner sections 140 may be attached and detached from the supply section 120. In this embodiment, the inner section 140 comprises an inner section connector 480. The inner section connector 480 connects with the cannula connector 130 via the Luer-lock connection 200 that was used to connect to the cannula handle 310 in the previous embodiment. The inner section connector 480 also comprises another Luer-lock connection 475 for connection to the cannula handle 310. The inner section connector 480 further comprises a second flangeless adapter 420 to provide a precise and smooth transition from the cannula connector 130 to the inner section 140. With reference to FIG. 5, preferably the second flangeless adapter 420 defines a chamber 440 and a radial lip 450. The chamber 440 further defines an input end 442, an output end 444 and a transition region 446. To effect a precise and smooth transition from the cannula connector 130 to the chamber 440, the output end 477 of the chamber 240 of the cannula connector 130 abuts with the input end 442 of the second chamber 440. The input end 442 of the second chamber 440 has an inner diameter that is substantially the same inner diameter of the output end 477 of the chamber 240 of the cannula connector 130. It will be appreciated that multiple sizes of inner sections may be attached to a single sized supply section because each inner section connector contains a particularly tapered transition region 446 that is suitable to smoothly transition the supply section 120 with an inner section 140.

Regardless of an exact configuration, the assembled curable material delivery system (such as the curable material delivery system 5 of FIG. 1) in accordance with principles of the present invention is highly useful in performing a wide variety of bone stabilizing procedures as part of an overall curable material delivery system. Using a vertebroplasty as a non-limiting example, in operation, the cannula 30 and stylet (not shown) are driven into the vertebra 40 to reach the trabecular cavity of the vertebra 40. The stylet is removed, leaving an open lumen 325 within the cannula 30. Curable material is mixed and loaded into the injector 10. Preferably, curable material is transferred under pressure from the injector 10 to the terminal end 144 of the inner section 140 prior to insertion of the inner section 140 into the lumen 325 of the cannula 30. In practice, an operator may advance curable material beyond the terminal end 144 of the inner section 140 in order to completely fill the inner section 140 and then wipe the terminal end 144 of the inner section 140 of excess curable material before insertion into the cannula 30. The carrier assembly is thus preloaded with curable material before the carrier assembly 20 is connected with the cannula 30 and the inner section 140 is inserted into the cannula 30. Once the inner section 140 is inserted into the cannula 30 and the carrier assembly 20 is connected with the cannula 30, curable material is immediately available to be delivered into the vertebra 40. This preloading step advantageously reduces the time required to deliver curable material into a patient because it can be done at substantially the same time the cannula 30 is being driven into the vertebra. In the prior art, the transfer of curable material from the injector can begin only after a supply tube is connected with the cannula. Time is thus required to transfer curable material from the injector to the supply tube, through the cannula tube, and into the patient. In the preferred embodiment of the present invention, however, curable material is preloaded to the terminal end 144 of the inner section 140 and the inner section 140 is then inserted into the cannula 30, thus making curable material immediately available to be delivered to the patient. One skilled in the art will realize, however, that curable material need not be preloaded into the carrier assembly to realize other advantages on the present invention.

At this point in the procedure, the inner section 140 is inserted into the cannula 30 and locked into place with the Luer-lock that connects the carrier assembly 20 to the cannula 30 in order to prohibit ejection of the carrier assembly 20 from the cannula 30 under pressure. The present invention permits burst-free injection of the curable material into an injection site at the beginning of the procedure because the carrier assembly 20 is primed prior to insertion into the cannula 30. When the physician activates the injector 10, the curable material is already going into the injection site and hence the flow is more predictable. The injector will then allow transfer of finely controlled amounts of curable material into the patient.

Following the delivery of a predetermined amount of curable material into the vertebra, the carrier assembly 20 may be detached from the cannula 30 and removed. It will be appreciated by one skilled in the art that when the carrier assembly 20 is removed, the inner section 140, which is loaded with curable material, is also removed and thus removes the column of curable material from the cannula 30. Several advantages are therefore realized in this embodiment. First, because the inner section 140 functions as a liner between the curable material and the cannula 30, there is no residual curable material inside of the cannula 30. The cannula 30 may therefore again be used to deliver additional material to the vertebra. Second, in the prior art, curable material may begin to set within the cannula 30 before completion of the procedure. When the procedure is complete and the cannula is removed, the resulting curable material column may break at a point inside the cannula 30 and not at the tip of the distal end 330 of the cannula 30. This results in a "spike" of curable material that is still attached to the curable material that has been deposited inside of the vertebra and the "spike" may extend outside of the vertebra. In the present invention, it has been observed that the curable material more uniformly breaks at the tip of the terminal end 144 of the inner section 140 when the inner section 140 is removed, thus minimizing the opportunities for curable material "spikes." Additionally, it is understood in the art that curable material will begin to set more quickly when exposed to body temperature. In the present invention, if delivery of curable material needs to be interrupted for a period of time, the inner section 140 can be conveniently temporarily removed from the cannula 30 and cooled by the relatively cooler room temperature, slowing the setting of the curable material. This is not possible under the prior art where curable material filled within the cannula 30 cannot be removed during the operation.

The present invention also allows a physician to conveniently fill multiple cannulas in one or more vertebra with curable material in the same operation. It is understood that a physician may enter a vertebral body with two basic approaches: uni-pedicular and bi-pedicular. In the uni-pedicular approach, the physician attempts to place the cannula in such a way that it traverses the midline of the vertebral body. This is done so that the entire vertebra can be filled through one entry point and one cannula. This technique can provide faster curable material filling, thus reducing procedure time. The technique, however, can be technically more challenging for the physician and may not always be possible to use. The bi-pedicular approach relies on placing a cannula through each pedicle of a vertebra. Because there is no need to traverse the midline of the vertebral body, the bi-pedicular approach is considered technically easier and safer. It permits equal filling on both sides of the vertebra, thus providing more uniform distribution of curable material.

The present invention can be used with both the uni-pedicular and bi-pedicular approaches. In the bipedicular approach the same carrier assembly 20 can be used to fill a first side of a vertebral body through a first cannula until the first side is satisfactorily filled. The inner section 140 of the carrier assembly 20 can then be removed from the first cannula and positioned within a second cannula to the other side of the vertebral body. It will be appreciated that upon removal of the carrier assembly 20, the first cannula is substantially free of curable material. It will also be appreciated that the inner section 140 is still filled with curable material and is thus "preloaded" with respect to the second procedure. Filling of the second side of the vertebral body can therefore immediately begin while the curable material begins to set on the first side. If the physician so desires, he or she can return to the first cannula and resume filling the first side. In a preferred embodiment, the physician can alternate between first and second cannula in a procedure, keeping both clean.

In another preferred embodiment, the physician may fill two different vertebral bodies in one procedure. The technique allows the physician to work between cannulas at various times while keeping the cannulas clean. In this embodiment, the physician drives cannulas into two or more vertebra. The carrier assembly 20 is preloaded with curable material as described above. The carrier assembly 20 is connected with the first cannula 30 for the first procedure and curable material is immediately delivered to the vertebra. At the completion of the first procedure, the carrier assembly 20 is removed from the first cannula 30. It will be appreciated that the inner section 140 is still filled with curable material and is thus "preloaded" with respect to the second procedure. The carrier assembly 20 is connected to the second cannula 30 and curable material is ready to be immediately delivered to the vertebra.

Figure 6:
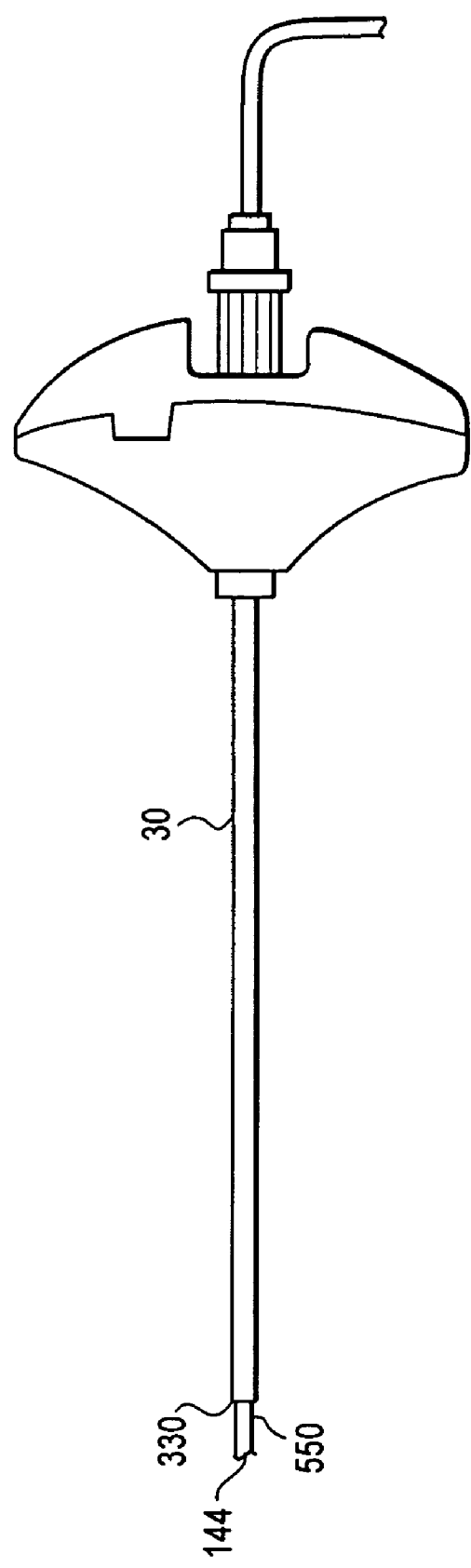
FIG. 6 is a perspective view of the curable material delivery device according to a preferred embodiment of the present invention after insertion of the inner section into the cannula.

Alternative structures may be employed within the scope of the present invention. With reference to FIG. 6, in another preferred embodiment, the terminal end 144 of the inner section extends beyond the distal end 330 of the cannula 30. The tip portion 550 of the terminal end 144 can contain different configurations to deliver curable material to an injection site.

Figure 7:
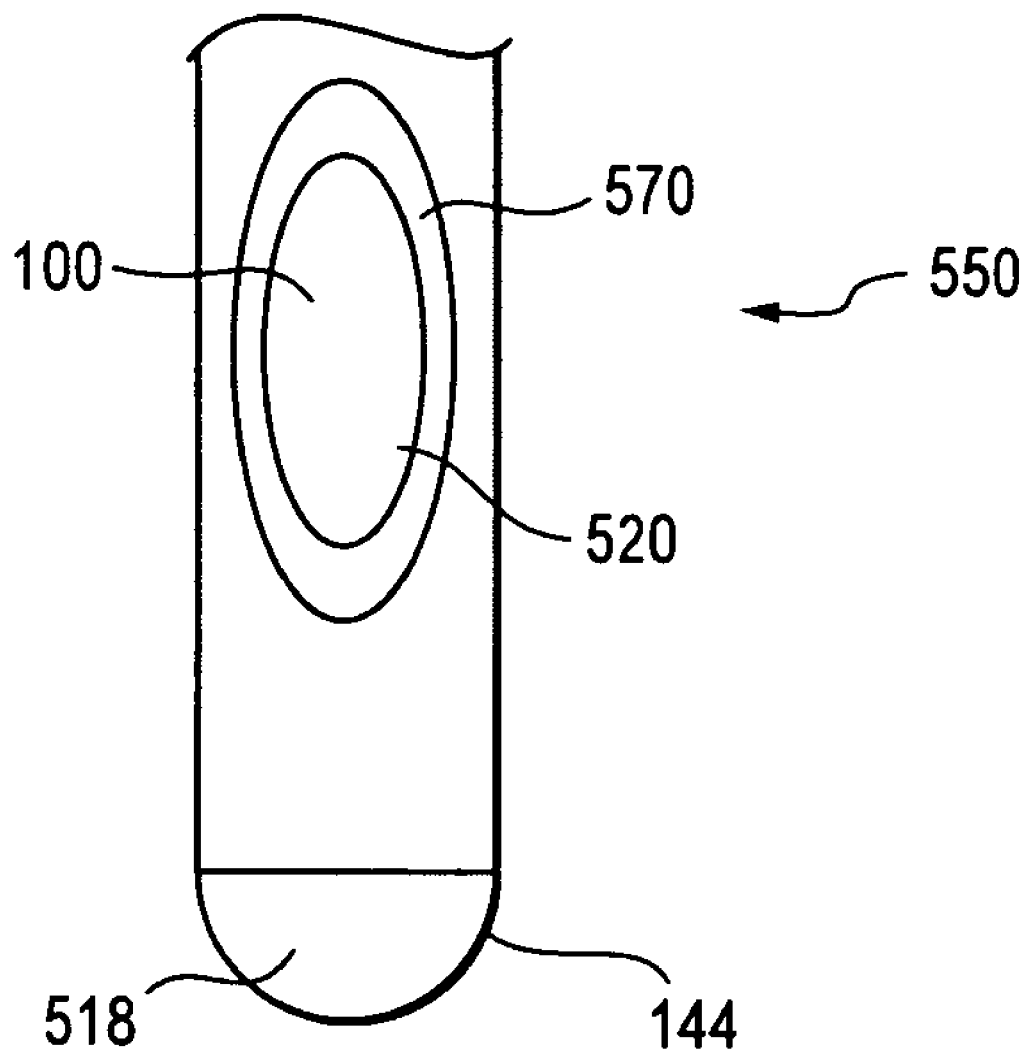
FIG. 7 is a perspective view of the tip portion of the curable material delivery device according to a preferred embodiment of the present invention.

In a preferred embodiment shown in FIG. 7, the tip portion 550 contains a closed, blunt end 518 such that the terminal end 144 is axially closed to the lumen 100 (i.e., material cannot be axially expelled from the terminal end 144 relative to an axis of the lumen 100). That is to say, material in the lumen 100 cannot be forced distally therefrom in an axial fashion. Further, the terminal end 100 defines or includes a blunt end 518. In one embodiment, the blunt end 518 defines a hemispherical surface, although other blunt (i.e., curved or curvilinear) shapes or contours are also acceptable. The blunt end 518 is adapted to provide a non-traumatic surface suitable for accessing, contacting and probing bone or tissue while minimizing the risk of puncture and/or coring of the tissue or damage to the bone.

Figure 8:
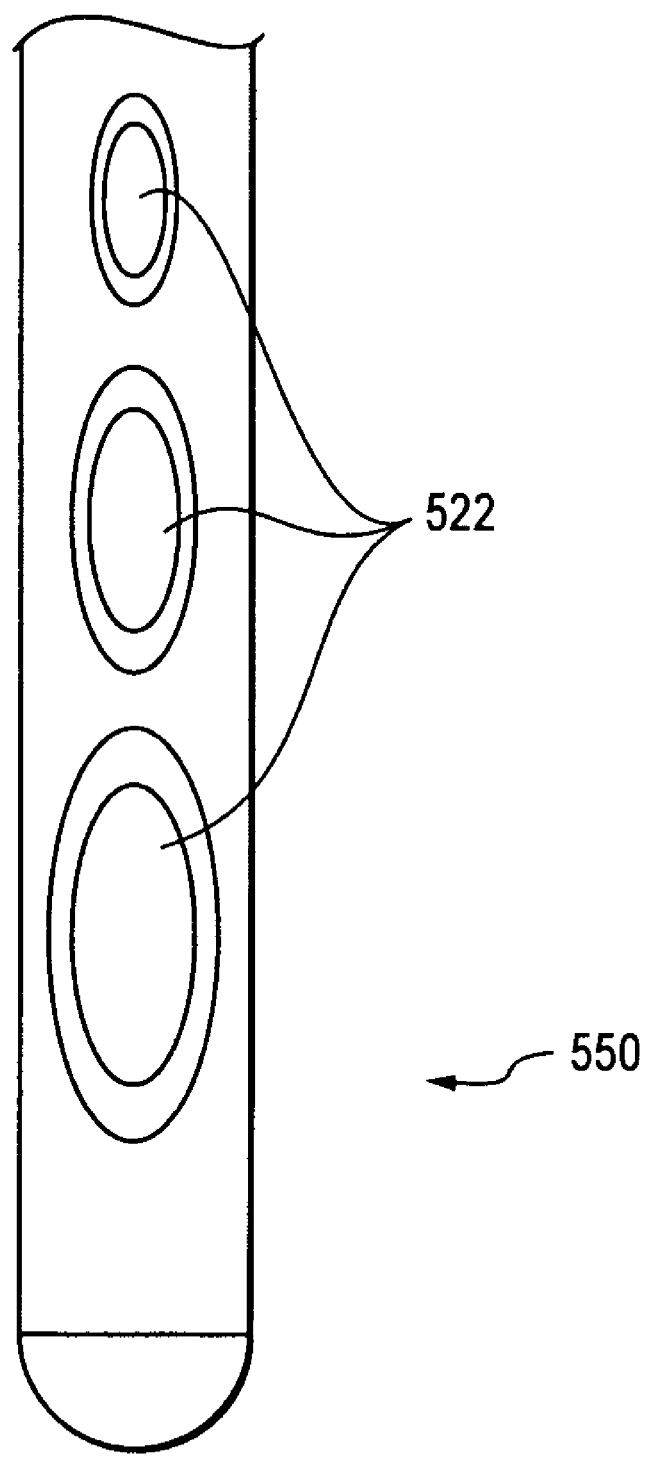
FIG. 8 is a perspective view of the tip portion of the curable material delivery device according to another preferred embodiment of the present invention.

The tip portion 550 also defines a side orifice 520 formed adjacent the terminal end 144, extending through a thickness of a sidewall of the tip portion 550. The side orifice 520 can assume a wide variety of shapes and sizes. For example, the side orifice 520 can be oval, circular, curvilinear, etc. In one embodiment, a chamfered region 570 can be formed about the side orifice 520 to eliminate sharp edges along an exterior of the tip portion 550 as well as to promote consistent flow of curable material from the side orifice 520 (via the expanding orifice size effectuated by the chamfered region 570). Although the tip portion 550 has been described as including or otherwise forming one side orifice 520, two, circumferentially aligned side orifices can be provided With reference to FIGS. 8-9, a variety of other configurations for the tip portion 550 are also acceptable. FIG. 8 shows a tip portion 550 having three side orifices 522 having consecutively smaller side orifices. This reduction in side orifice size proximal the terminal end 144 promotes consistent distribution of curable material otherwise being forced through the tip portion 550. While three of the side orifices 522 are shown, other configurations are also acceptable. For example, multiple side orifices (i.e., more than three side orifices) can be formed longitudinally along the length of the tip portion 550, and in addition, the side orifices can include more than one longitudinally aligned series of side orifices. In an exemplary embodiment, the side orifices that are visible in FIG. 8 are matched by another column of longitudinally aligned side orifices formed on an opposing side of the tip portion 550 (and therefore not visible in the view of FIG. 8). Aspects of the present invention provide for the side orifices 522 to define circular side orifices, non-circular side orifices, or a set of circular and non-circular side orifices.

Figure 9:
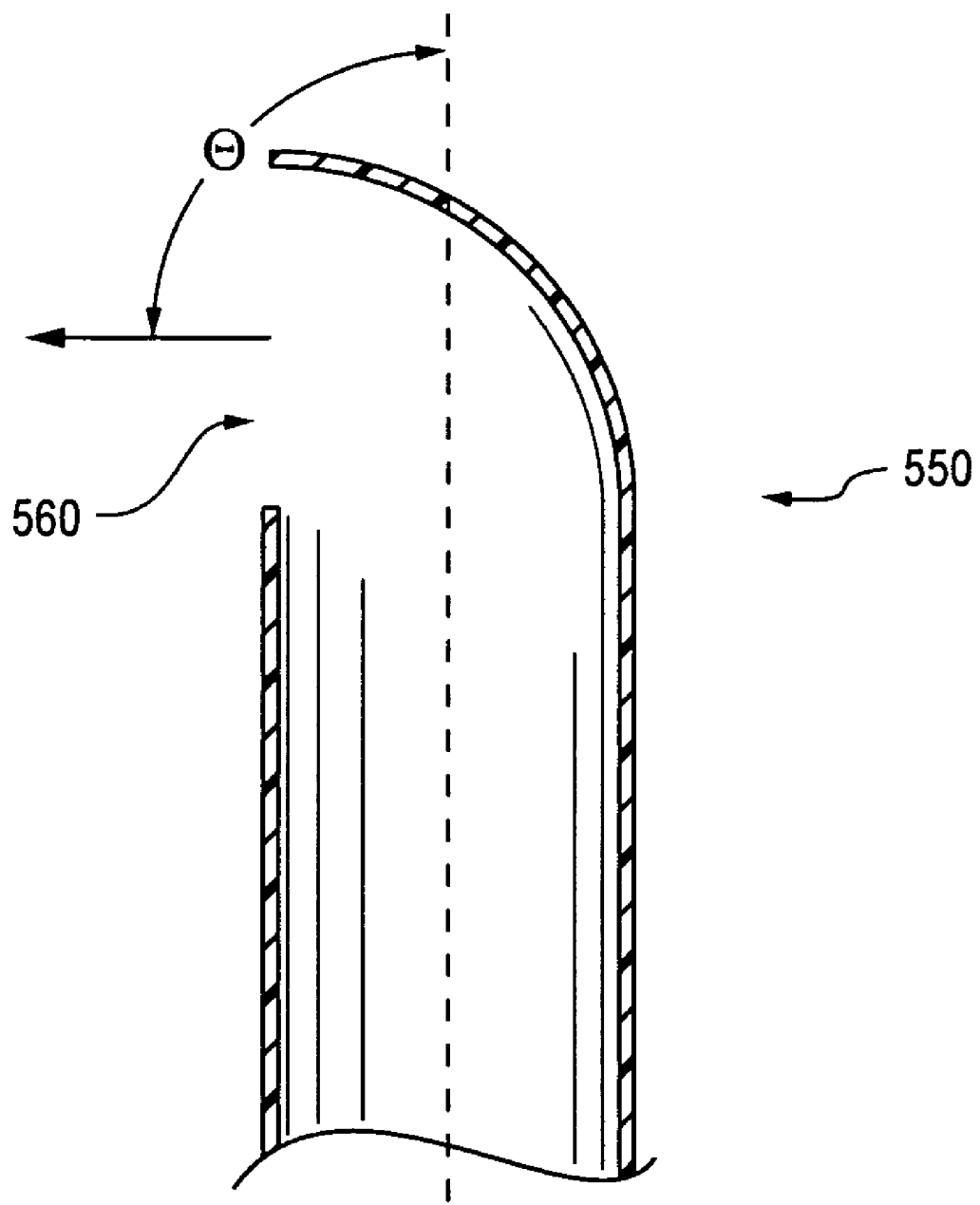
FIG. 9 is a perspective view of the tip portion of the curable material delivery device according to another preferred embodiment of the present invention.

FIG. 9 shows another preferred embodiment of the tip portion 550. In this embodiment, the tip portion 550 is bent to provide approximately a 90 degree opening 560 with respect to the axis of the inner section 140. In the exemplary embodiment, the angle between the opening 560 and the axis of the inner section, represented by θ, is 90 degrees. Aspects of the present invention contemplate that the angle θ may be between 0 and 90 degrees and is preferably substantially 90 degrees. Preferably, the leading edge of the tip portion 550 should be substantially rounded so that the tip portion 550 does not easily cut into tissue. In one embodiment, the inner section comprises a rotatable hub that rotates the inner section 140. The hub would comprise a visual indicator corresponding the orientation of the opening 560 so that the clinician may visualize the opening at the terminal end of the inner section. Preferably, the hub of the inner section has a seal to allow the hub to be rotated 360 degrees. Therefore, the clinician can orient cement injection in any direction based upon the architecture of the area that the bone cement in injected into.

Figure 10:
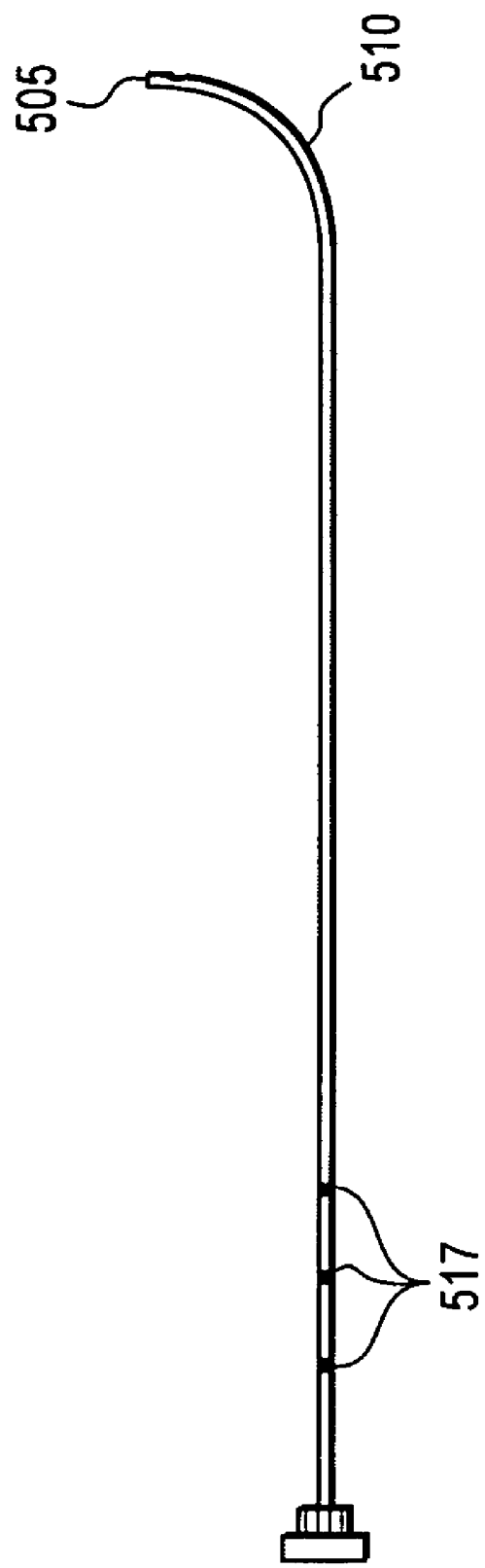
FIG. 10 is a perspective view of the curable material delivery device according to a preferred embodiment of the present invention.

With reference to FIG. 10, another preferred embodiment of the present invention comprises a curved portion 510 at the terminal end 505 of the inner section that extends beyond the distal end of the cannula 30 during a procedure. In this embodiment, the curved portion 510 is a resilient preformed curved section capable of being straightened for insertion through the elongated tubular portion of the cannula. The curved portion also has a shape memory feature which allows it to return to its curved shape after exiting the distal end of the elongated tubular portion. The curved portion 510 may be formed integrally with the inner section or may be a separate structure that is bonded with the inner section. In a preferred embodiment, a visual indicator, such as a symbol or color indicator on the cannula connector, for example, is provided to indicate to the physician the orientation of the curved portion 510 relative to the cannula connector. The inner section 140 includes indicia 517 adjacent the terminal end 144. The indicia 517 is indicative of a location of the terminal end 144 relative to the distal end of the cannula 30. The indicia 517 can assume a wide variety of forms differing from that shown in FIG. 10, and in some embodiments can be eliminated. The end portion 550 may be any of the tip configurations described above.

In operation, a cannula is positioned within a vertebral body as described above. The carrier assembly having the curved portion 510 is preloaded with curable material and inserted into the elongated tubular portion of the cannula. Depth indicia 517 on the inner section may be used by the physician to determine how far the curved portion 510 has traveled beyond the distal end of the cannula 30. After the desired depth is achieved, curable material may be delivered to the vertebral body. Using the visual indicator of the orientation of the curved portion 517, the curved portion 515 may be repositioned so that curable material may be delivered to different areas within the vertebral body. Following the delivery of a predetermined amount of curable material into the vertebra, the carrier assembly 20 is removed from the cannula 30.

It is also contemplated that according to another preferred embodiment, the invention may be used with a tamping operation using an inflatable device. Tamping operations using a balloon are known in the prior art and are disclosed at, for example, U.S. Pat. No. 4,969,888, titled "Surgical Protocol for Fixation of Osteoporotic Bone Using Inflatable Device" and U.S. Pat. No. 5,108,404, titled "Surgical Protocol For Fixation of Bone Using Inflatable Device." In those procedures in which physicians believe a clinical advantage can be gained by tamping the internal bone, the present invention may be used in the following manner. First, a physician gains entry into the bone using a cannula and stylet combination. After gaining entry, the trabecular bone is morcellated to create a void for the tamping device. The tamping device is inserted into this space and expanded, thus enlarging the void in the bone. After the tamping device is removed, the preloaded inner section is inserted into the cannula and curable material is delivered into the site as already described.

It is therefore intended that the foregoing detailed description be regarded as illustrative rather than limiting, and that it be understood that it is the following claims, including all equivalents, that are intended to define the spirit and scope of this invention. In this regard, it should be understood that although reference to bone sites and curable material has been made, the devices and methods disclosed herein are not limited in application to bone sites and curable materials. One skilled in the art will understand that the devices and methods disclosed herein may be used at non-bone sites such as spinal discs and may be used to inject material other than curable material.

INDUSTRIAL APPLICABILITY

The system and method answers a long felt need for increasing safety and control in the administration of curable material to a bone site by providing an inner section of tubing within a cannula that may be preloaded with curable material. The inner section of tubing allows a cannula to remain free of the curable material so that it may be reused during the procedure. Additionally, preloading the inner section of tubing with curable material allows for reduced time to deliver curable material to a patient and increases control over the curable material delivery.

What is claimed is:

1. An apparatus for introducing material into an injection site of a patient comprising:
   a cannula defining a lumen;
   a carrier for delivering material from an injector to an injection site, the carrier defining a lumen and the carrier comprising
   a supply section operable to receive curable material, and an inner section having an axis and defining a tip section operable to direct material in a direction that is off-axis relative to the axis of the inner section, wherein the carrier is releasably attachable with the cannula, and at least a portion of the inner section is located within the lumen of the cannula, wherein said portion is at least 50% the length of the cannula.

2. The apparatus of claim 1 wherein the tip section defines at least one orifice for delivering material.

3. The apparatus of claim 1 wherein the tip section defines at least two orifices for delivering material wherein the orifices at least two of the orifices are of different size.

4. The apparatus of claim 1 wherein the cannula is connected with a handle having a connector operable for attaching the carrier.

5. The apparatus of claim 1 wherein the carrier further comprises a connector operable for attaching to the cannula.

6. The apparatus of claim 1 wherein the supply section is a tube having a first end and a second end and the inner section is a tube having a first end and a second end.

7. The apparatus of claim 6 wherein the carrier further comprises a connector for connecting an end of the supply section with an end of the inner section wherein the connector defines a chamber between an end of the supply section and an end of the inner section.

8. The apparatus of claim 7 wherein the supply section, chamber and inner section form a lumen section having walls defining a substantially smooth transition from the supply section to the inner section.

9. The apparatus of claim 8 wherein the supply section and inner section have inner diameters that are different and an inner wall of the chamber is tapered to form a transition from a first diameter to a second diameter.

10. The apparatus of claim 9 wherein a first end the supply section connects with an injector containing a volume of material.

11. The apparatus of claim 6 wherein the supply section and inner section are made of non-compliant materials.

12. The apparatus of claim 1 wherein the tip section directs material at an angle between 45 and 90 degrees from the axis of the inner section.

13. An apparatus for introducing material into an injection site of a patient comprising:
an injector containing a volume of material;
a cannula having an elongated portion defining a lumen wherein an end of the elongated portion is configured for positioning within the injection site;
a carrier defining a lumen between the injector and the injection site, the carrier further comprising
a supply tube having a first end adaptable for connecting the supply tube with the injector and receiving material from the injector, the supply tube further having a second end;
a connector attaching the carrier with the cannula, the connector also defining a chamber; and
an inner tube having a first end and a second end, wherein the connector connects the second end of the supply tube with the first end of the inner tube via a chamber such that the supply tube, chamber and inner tube form a lumen having a substantially smooth transition from the supply tube to the inner tube, and at least a portion of the inner tube is located within the lumen of the elongated portion of the cannula, wherein said portion extends through at least 50% the length of the elongated portion of the cannula.

14. The apparatus of claim 13 wherein the second end of the inner tube defines a tip section having a blunt end and at least one orifice for delivering material.

15. The apparatus of claim 14 wherein the tip section defines at least two orifices for delivering material wherein the orifices at least two of the orifices are of different size.

16. A method of delivering material to the injection site comprising the steps of:
inserting a cannula defining an elongated lumen into an injection site;
connecting a carrier defining a lumen with an injector containing a volume of material;
pre-loading the lumen of the carrier with the material so that the material is delivered to a distal end of the carrier from the injector, wherein the carrier is thus pre-loaded with material;
inserting at least a portion of the distal end of the pre-loaded carrier into the elongated lumen of the cannula such that the portion extends through at least 50% the length of the elongated lumen; and
delivering material to an injection site.

17. The method of claim 16 further comprising the steps of removing the carrier from the cannula after delivering material to the injection site wherein the carrier is pre-loaded to deliver material to a second injection site and inserting at least a portion of the distal end of the pre-loaded carrier into an elongated lumen of a second cannula to deliver curable material to the second injection site.

18. The method of claim 17 wherein the injection site and second injection site are within a vertebra.

19. The method of claim 16 wherein the carrier is a single tubular structure.

20. The method of claim 16 wherein the carrier defines a tubular supply section and a tubular inner section wherein the inner section and supply section are of different diameters.

21. The method of claim 16 wherein the elongated lumen of the cannula defines an axis and material is delivered to the injection site in a direction that is not coaxial with the axis of the elongated lumen of the cannula.

22. A method of delivering material to the injection site comprising the steps of:
inserting a cannula defining an elongated lumen into an injection site;
connecting a carrier with an injector containing a volume of material, said carrier defining a lumen and comprising an inner section distal from the injector;
inserting at least a portion of the distal inner section of the carrier into the elongated lumen of the cannula such that the portion extends through at least 50% the length of the elongated lumen;
transmitting material from the injector through the lumen of the carrier wherein curable material is also transmitted through the distal inner section; and
delivering material to an injection site.

23. The method of claim 22 further comprising the steps of removing the carrier from the cannula after delivering material to the injection site and inserting at least a portion of the distal inner section of the carrier into an elongated lumen of a second cannula to deliver curable material to a second injection site.

24. The method of claim 23 wherein the injection site and second injection site are within a vertebra.

25. The method of claim 23 wherein the injection site is within a first vertebra and a second injection site is within a second vertebra.

* * * * *